(12) United States Patent
Jagelski et al.

(10) Patent No.: US 10,383,652 B2
(45) Date of Patent: Aug. 20, 2019

(54) TISSUE MANIPULATION TOOL

(71) Applicant: Boston Scientific Scimed, Inc., Maple Grove, MN (US)

(72) Inventors: Matthew R. Jagelski, West Roxbury, MA (US); John Golden, Norton, MA (US); Melissa Horton, Watertown, MA (US); Erin Zinkus, Spencer, MA (US); Gary Pirani, Holden, MA (US); Ellen Kaplan, Irvine, CA (US); Briana Moretti, Smithfield, RI (US); Jennifer Saunders, Westport, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 160 days.

(21) Appl. No.: 15/381,354

(22) Filed: Dec. 16, 2016

(65) Prior Publication Data

US 2017/0172601 A1    Jun. 22, 2017

Related U.S. Application Data

(60) Provisional application No. 62/269,489, filed on Dec. 18, 2015.

(51) Int. Cl.
*A61B 17/3203*    (2006.01)
*A61B 17/3205*    (2006.01)
(Continued)

(52) U.S. Cl.
CPC ...... *A61B 17/3203* (2013.01); *A61B 1/00068* (2013.01); *A61B 1/00087* (2013.01);
(Continued)

(58) Field of Classification Search
CPC .......... A61B 2017/00269; A61B 2017/00296; A61B 2017/306; A61B 17/00234;
(Continued)

(56) References Cited

U.S. PATENT DOCUMENTS 8,574,186 B2    11/2013  Fischer
8,979,836 B2    3/2015   Fischer et al.
(Continued)

OTHER PUBLICATIONS

International Search Report and Written Opinion of the International Search Authority dated Jun. 22, 2017, issued in corresponding International Application No. PCT/US2016/067270, filed Dec. 16, 2016 (14 pages).

*Primary Examiner* — Ryan J. Severson
*Assistant Examiner* — Mohamed G Gabr
(74) *Attorney, Agent, or Firm* — Bookoff McAndrews, PLLC

(57) ABSTRACT

A medical device for manipulating a portion of tissue. The device may have one or more opposing jaws. One of the jaws may be configured to be placed between the portion of tissue and an underlying portion of tissue, and have an orifice configured to direct a fluid towards a surface of the other jaw so as to move the portion of tissue towards the said other jaw. A fluid delivery channel may extend between the orifice and a fluid source. A switch may be operable to flow the fluid from the source, through the channel, and out of the orifice. Related methods are also disclosed.

20 Claims, 5 Drawing Sheets

(51) Int. Cl.
  *A61B 1/00* (2006.01)
  *A61B 1/015* (2006.01)
  *A61B 90/00* (2016.01)
  *A61B 17/00* (2006.01)
  *A61B 17/32* (2006.01)
  *A61B 1/018* (2006.01)

(52) U.S. Cl.
  CPC ...... *A61B 1/00089* (2013.01); *A61B 1/00091* (2013.01); *A61B 1/00101* (2013.01); *A61B 1/00119* (2013.01); *A61B 1/00121* (2013.01); *A61B 1/00128* (2013.01); *A61B 1/015* (2013.01); *A61B 1/018* (2013.01); *A61B 17/00234* (2013.01); *A61B 17/32* (2013.01); *A61B 17/320016* (2013.01); *A61B 90/03* (2016.02); *A61B 17/32056* (2013.01); *A61B 2017/00269* (2013.01); *A61B 2017/00907* (2013.01); *A61B 2017/32035* (2013.01); *A61B 2017/320044* (2013.01); *A61B 2090/036* (2016.02)

(58) Field of Classification Search
  CPC ...... A61B 17/32056; A61B 17/320016; A61B 17/3202; A61B 17/3478; A61B 17/0469; A61B 17/221; A61B 17/320036; A61B 17/32037; A61B 1/018; A61B 1/00089; A61B 1/00101; A61B 1/00094; A61B 18/14; A61B 18/1477; A61F 2/0036; A61F 2/20; A61M 2025/0035; A61M 25/0023; A61M 25/003
  See application file for complete search history.

(56) References Cited

U.S. PATENT DOCUMENTS

| | | | |
|---|---|---|---|
| 2006/0069304 A1* | 3/2006 | Takemoto | A61B 1/00087 600/104 |
| 2006/0100569 A1 | 5/2006 | McRury et al. | |
| 2006/0100614 A1 | 5/2006 | Long | |
| 2008/0207994 A1 | 8/2008 | Gonon | |
| 2009/0069805 A1 | 3/2009 | Fischer et al. | |
| 2009/0125027 A1* | 5/2009 | Fischer | A61B 17/3203 606/46 |
| 2009/0149712 A1* | 6/2009 | Fischer | A61B 17/3203 600/156 |
| 2013/0331855 A1* | 12/2013 | Smith | A61B 17/221 606/114 |
| 2014/0012301 A1* | 1/2014 | Wilson | A61B 90/02 606/170 |
| 2014/0066707 A1 | 3/2014 | Muyari et al. | |
| 2014/0276790 A1 | 9/2014 | Raybin et al. | |

* cited by examiner

TISSUE MANIPULATION TOOL

CROSS-REFERENCE TO RELATED APPLICATIONS

This patent application claims the benefit of priority under 35 U.S.C. § 119 to U.S. Provisional Patent Application No. 62/269,489, filed Dec. 18, 2015, which is herein incorporated by reference in its entirety.

TECHNICAL FIELD

Aspects of the present disclosure generally relate to medical devices and procedures. In particular, aspects of the present disclosure relate to medical devices for manipulating a portion of tissue associated with an organ or other body part.

BACKGROUND

Elongated tools are often used within a variety of diagnostic and surgical procedures, such as ureteroscopy, endoscopy, laparoscopy, arthroscopy, gynoscopy, thoracoscopy, and cystoscopy, etc. Many of these procedures are carried out for purposes of tissue resection, which generally includes removal of a portion of tissue from an organ or a gland to treat tumors, infestations, and the like. Such procedures are typically carried out by inserting one or more elongated tools into the body through a surgical incision or natural anatomical orifice (e.g., mouth, vagina, or rectum), and using said tools to perform a procedure.

Endoscopic Mucosal Resection (EMR) and Endoscopic Sub-mucosal Dissection (ESD) are two exemplary types of said procedures, wherein an elongated tool, such as an endoscope, is used to resect a lesion from a portion of tissue (e.g., a mucosa or surface layer) that is attached to an underlying portion of tissue (e.g., a submucosa or underlying layer of dense irregular connective tissue). A cutting tool, such as a blade, snare, wire loop, or like tool, is typically extended from a working channel of the endoscope to perform the resection. Because these cutting tools are deployed within a living body, there remains a constant risk of inadvertently damaging otherwise healthy tissue. These potential complications can increase the amount of time required to complete the procedure, thereby increasing the cost of the procedure and the potential for infection.

SUMMARY

Aspects of the present disclosure related to a medical device, and associated methods, for manipulating a portion of tissue are now described In one example, the device may comprise a distal end with a first jaw having a first surface and a second jaw having a second surface, the second surface may be opposite of the first surface about an axis and configured to be placed between the portion of tissue and an underlying portion of tissue; and an orifice may be defined by the second surface and configured to direct a fluid towards the first surface so as to move the portion of tissue towards the first surface.

This example may additionally and/or alternatively comprise one or more of the following features: a position of the first jaw may be fixed relative to a position of the second jaw; the orifice may have at least one nozzle that forms the fluid into a jet; the second jaw may have a distal edge configured to guide a proximal end of said portion of tissue over the jet when the device is moved distally; the jet may have a direction of travel that is transverse to the axis so as to force the portion of tissue towards the first surface; the jet may apply a tensile force to the portion of tissue by moving the proximal end of said portion in the direction of travel; the first and second jaws may be integral with a cap having an adapter that is attached to at least one other medical device; at least a portion of the cap may be formed of a transparent material, and the adapter may be formed of an elastomeric material; a fluid delivery channel may extend between the orifice and a fluid source; a switch may be operable to flow the fluid from the source, through the delivery channel, and out of the orifice; the switch may have a frame attached to at least one other medical device; the at least one other medical device may be an endoscope; the adapter and the frame may be removably attached to the endoscope; the device may have a proximal end with an opening sized to receive a cutting tool; the cutting tool may be a blade or a snare.

In another example, the device may comprise a distal end with a first jaw having a first surface and a second jaw having a second surface, the first surface may be opposite of the second surface along an axis so as to define a tissue receiving opening, the second surface may have a distal edge insertable between the portion of tissue and an underlying portion of tissue; and an orifice may be defined by the second surface and configured to direct a fluid towards the first surface so as to move the portion of tissue towards the first surface.

Additional aspects of this example may additionally and/or alternatively comprise one or more of the following features: a position of the first jaw may be fixed relative to a position of the second jaw; the distal edge may be configured to guide a proximal end of said portion of tissue into the receiving opening when the device is moved distally; the orifice may have one or more nozzles that form the fluid into a jet, and the distal edge may be configured to guide the proximal end of said portion of tissue over the jet; the one or more nozzles may be adjustable so as to vary the fluid pressure applied to the portion of tissue by the jet; the jet may a have direction of travel that is transverse to the axis so as to force the portion of tissue towards the first surface and apply a tensile force to the portion of tissue by moving a proximal end of said portion of tissue in the direction of travel; the first and second jaws may be integral with a cap having an adapter that is removably engageable with the distal end of at least one other medical device, and a proximal end with an opening sized to receive a cutting tool extending distally from said distal end; the first surface may be configured to direct the fluid proximally towards the opening; a fluid delivery channel may extend between the orifice and a fluid source, and a switch may be operable to flow the fluid from the source, through the delivery channel, and out of the orifice; and/or the fluid source may be operably attached to a fluid pump that is operated in response to the switch.

In yet another example, the device may be for resecting a portion of tissue. The device may comprise a distal end with a first jaw having a first surface and a second jaw having a second surface, the first surface may be opposite of the second surface about an axis, the second surface may have a distal edge configured to be placed between the portion of tissue and an underlying portion of tissue; an orifice may be defined by the second surface and configured to direct a fluid towards the first surface so as to move the portion of tissue towards the first surface; the device may also have a proximal end with an opening sized to receive a cutting tool; a fluid delivery channel may extend between the orifice and the proximal end for attachment to a fluid source; and/or a switch may be operable to flow the fluid from the source, through the delivery channel, and out of the orifice.

Additional aspects of this example may additionally and/or alternatively comprise one or more of the following features: the orifice may have one or more nozzles that form the fluid into a jet, and the distal edge may be configured to guide the proximal end of said portion of tissue over the jet; the first and second jaws may be integral with a cap having an adapter that is removably engageable with at least one other medical device and a proximal end with an opening sized to receive at least one tool extending proximally from a working channel of said other medical device; and/or at least one other medical device is an elongated tool or endoscope.

Another aspect of the present disclosure is a method of manipulating a portion of tissue. An example of this method may comprise placing a distal end of a device near the portion of tissue, the distal end may have a first jaw with a first surface and a second jaw with a second surface, the first surface may be opposite of the second surface about an axis, and an orifice may be defined by the second surface; guiding the portion of tissue over the orifice; and flowing a fluid out of the orifice towards the first surface so as to move the portion of tissue toward the first surface.

Additional aspects of this example may additionally and/or alternatively comprise one or more of the following: placing the second jaw between the portion of tissue and an underlying portion of tissue; puncturing the portion of tissue before the step of placing the second jaw between the portion of tissue and an underlying portion of tissue; cutting the portion of tissue away from the underlying portion of tissue after said portion of tissue has been moved toward the first surface; the portion of tissue may be cut by a cutting tool, and the device may have a proximal end with an opening sized to receive the cutting tool, such that the method further comprises the step of extending the cutting tool distally through the opening; and/or the first and second jaws may be integral with a cap having an adapter that is removably attachable with at least one other medical device, such that the method further comprises step of attaching the adapter to said other medical device.

It may be understood that both the foregoing summary and the following detailed description are exemplary and explanatory only, neither being restrictive of the disclosure claimed below.

BRIEF DESCRIPTION OF THE DRAWINGS

The accompanying drawings, which are incorporated in and constitute a part of this specification, illustrate exemplary embodiments that, together with the written descriptions, serve to explain the principles of this disclosure.

DETAILED DESCRIPTION

The present disclosure is now described with reference to exemplary embodiments of a tissue manipulation tool and associated methods. Some embodiments are described with reference to an elongated tool or endoscope used to perform an EMR or ESD procedure. Any reference to a particular tool or procedure is provided for convenience and not intended to limit the present invention, such that the concepts and novelty underlying each embodiment may also be utilized for any analogous type of device or procedure, medical or otherwise.

The directional terms "proximal" and "distal" are used herein to refer to the relative components and features of the present invention. The term proximal refers to a position closer to the exterior of the body or a user, whereas the term distal refers to a position closer to the interior of the body or further away from the user. A number of exemplary axes are also described with reference to these directional terms. For example, most of the embodiments depicted in FIGS. 1-5 are depicted with a "P" (for proximal) or "D" (for distal) arrow about an axis X-X to ensure consistent use of those terms. As before, these directional terms are provided for convenience and not intended to limit the present invention to a particular orientation.

Figure 1:
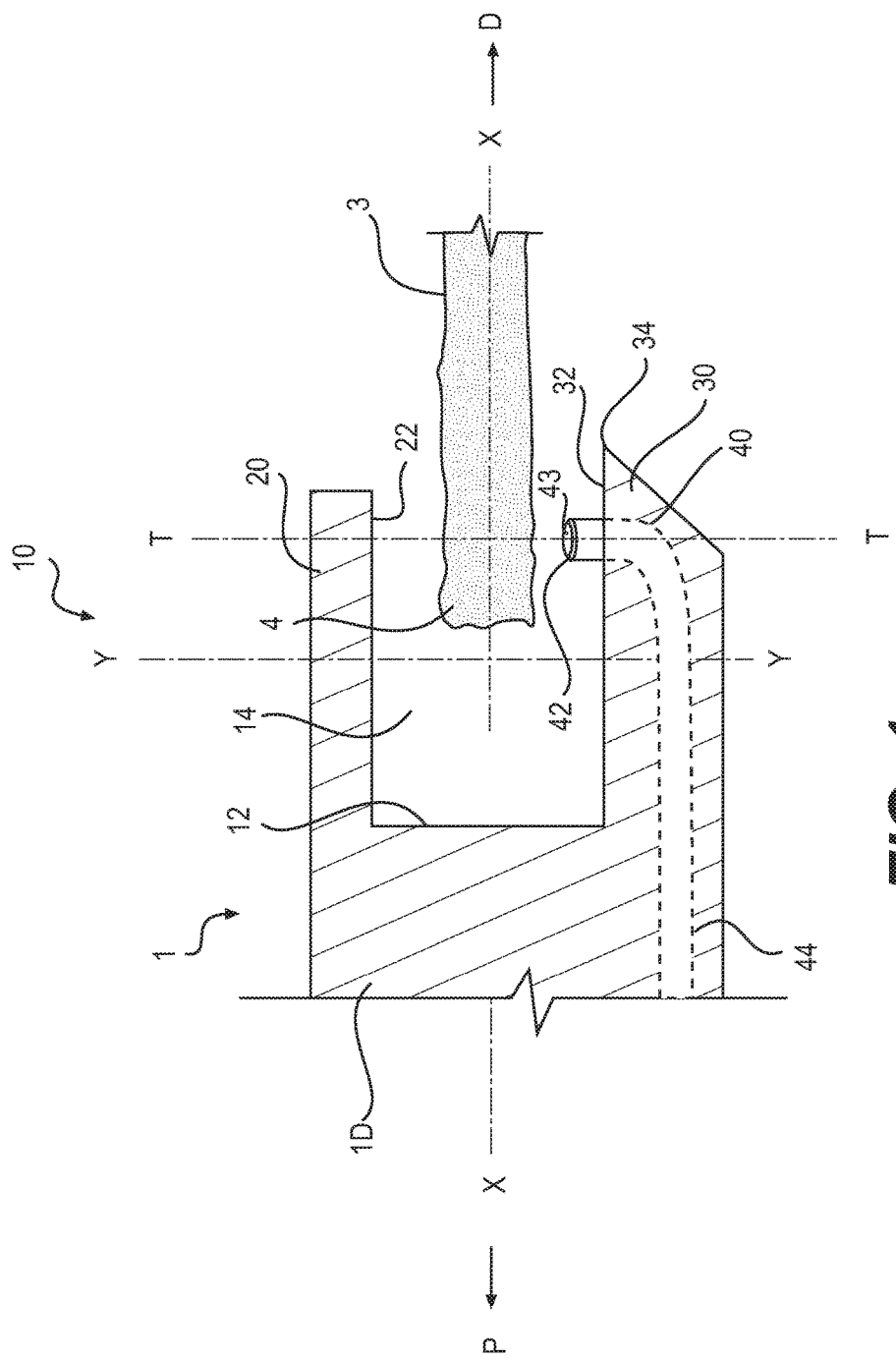
FIG. 1 depicts an exemplary embodiment of the present disclosure that is integral with a distal end of an elongated tool or endoscope.

One embodiment of the present disclosure is depicted in FIG. 1 as a device 10 attached to a distal end 1D of an elongated tool or endoscope 1. Device 10 is configured to manipulate a portion of tissue 3. As shown, device 10 has a first jaw 20 having a first or interior surface 22 and a second jaw 30 having a second or interior surface 32. First surface 22 is disposed opposite of second surface 32 along a normal axis Y-Y of device 10 that is transverse with a longitudinal axis X-X of endoscope 1. Surfaces 22 and 32 are adjoined by a distal face 12 so as to define a tissue receiving opening 14 of device 10. Opening 14 is sized to receive said portion of tissue 3 therein. Although not required, a position of first jaw 20 is fixed relative to a position of second jaw 30 in FIG. 1 to provide opening 14 with the substantially U-shaped profile.

An orifice 40 is defined by second surface 32 and configured to direct a fluid towards first surface 22 so as to move at least a proximal end 4 of portion of tissue 3 toward first surface 22. In the embodiment of FIG. 1, a nozzle 42 is mounted in orifice 40 and attached to a fluid delivery channel 44 that extends proximally inside of endoscope 1 towards a fluid source (not shown). Any type of fluid may be used, including any biocompatible fluid, such as water, saline, or the like. Nozzle 42 has a nozzle opening 43 with a diameter smaller than the corresponding diameter of fluid delivery channel 44 so as to form the fluid into a rapid stream or jet that flows along a direction of travel T-T when delivered to nozzle 42 under pressure. Direction of travel T-T is parallel to axis Y-Y in FIG. 1 and, in some embodiments, transverse to axis Y-Y.

The fluid source may be a water port that delivers a pressured flow of fluid to channel 44. For the embodiment of FIG. 1, a pump (not shown) is used to achieve the desired fluid pressure. The pump may be attached to endoscope 1 or located remotely therefrom. Said pump is operated by a switch (e.g., similar to switch 146 of FIG. 3A) that causes the fluid to flow from the source, through channel 44, and out of nozzle 42. Any type of switch, button, or other actuating device may be used. The fluid pressure applied to the proximal end 4 of said portion of tissue 3 by the jet is relative to the type of tissue. For esophageal or stomach tissue, the fluid pressure may be less then about 435 Pounds-force per square inch or "PSI" (or 30 Bar) to avoid puncturing or cutting portion of tissue 3. For the left colon, the fluid pressure may less than about 290 PSI (or 20 Bar); whereas, for the right colon, the fluid pressure may be less than 145 PSI (or 10 Bar). These values are, of course, exemplary. Because first surface 22 is disposed opposite of second surface 32 along axis Y-Y, first surface 22 acts as a shield to prevent the jet from damaging any otherwise healthy tissue beyond first jaw 20. First surface 22 may also act as a backstop against which the portion of tissue 3 rests, or upon which said portion of tissue 3 is pinned to by the jet.

Second surface 32 and a distal or second edge 34 of second jaw 30 are configured to guide the proximal end 4 of said portion of tissue 3 over nozzle 42. Distal edge 34 of FIG. 1 is sharpened so that device 10 may be moved distally to separate the proximal end 4 of said of portion tissue 3 away from an underlying portion of tissue 5 (e.g., FIGS. 4A-B). In complement, second surface 32 is contoured to guide the proximal end 4 of said portion of tissue 3 over nozzle 42 once separated from underlying tissue 5. Distal end 1D of endoscope 1 may be articulated to facilitate separation. Alternatively, distal edge 34 may be atraumatic (e.g., blunt) to avoid damaging, cutting, or separating portion of tissue 3 so that a distinct device may be used to separate it from underlying portion of tissue 5. Once portion of tissue 3 has been positioned over nozzle 42, the jet may be used to move at least proximal end 4 towards first surface 22 along directional of travel T-T. This configuration allows the jet to apply a tensile force to said portion of tissue 3 as its proximal end 4 is moved. This tensile force stabilizes portion of tissue 3 for resection. As described more fully below, the resection may be performed by any known cutting tool, including a blade, a snare, or the like.

Numerous alternative embodiments of device 10 are now described with reference to a device 110 and 210. Wherever possible, like reference numbers have been utilized to describe each feature of these alternative embodiments. Although certain features are described with reference to a particular embodiment, any embodiment may include any possible combination of these features.

Figure 2A:
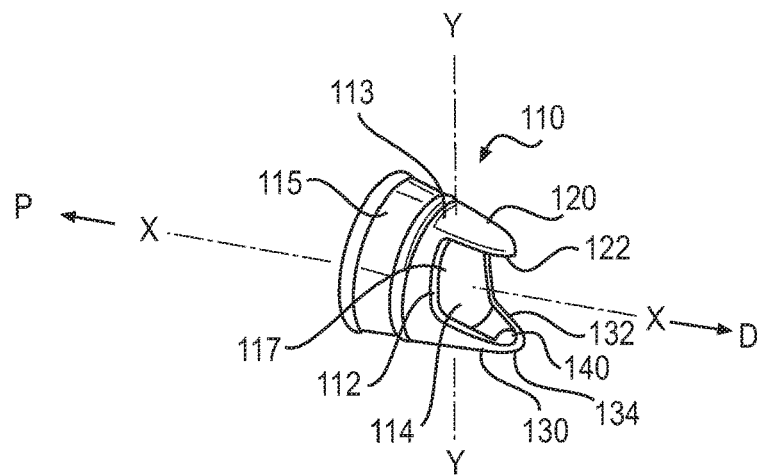
FIG. 2A depicts another exemplary embodiment of the present invention that is removably attachable to a distal end of an elongated tool or endoscope.
Figure 2B:
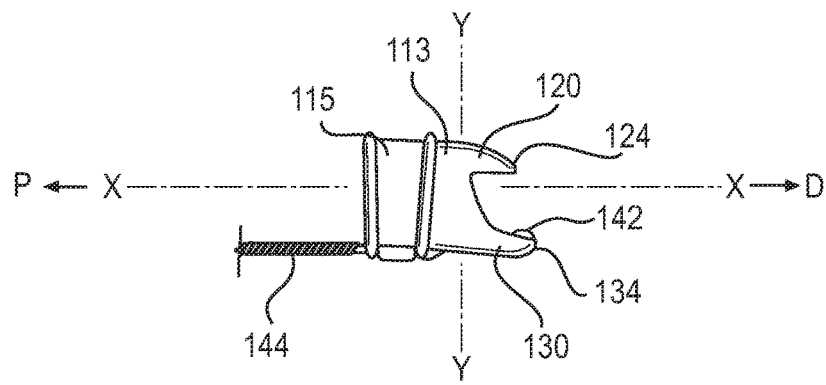
FIG. 2B depicts a side view of the embodiment of FIG. 2A.
Figure 2C:
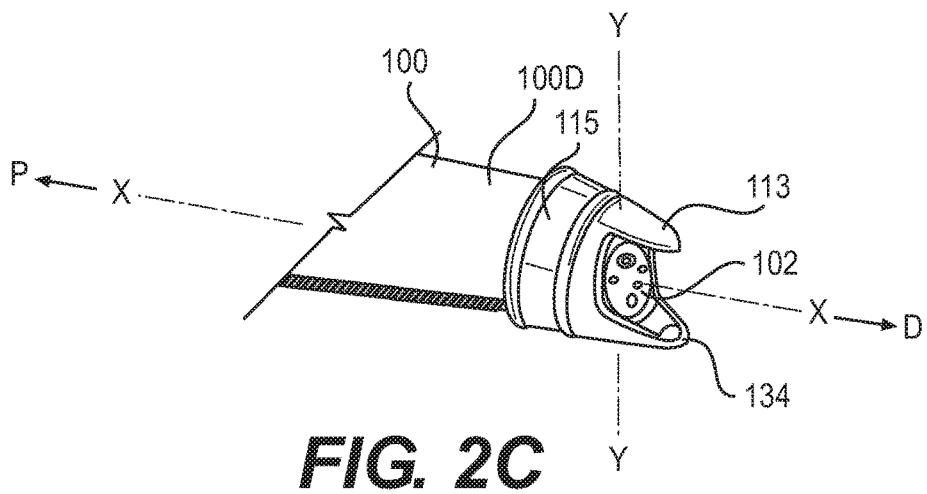
FIG. 2C depicts the embodiment of FIG. 2B after being removably attached to the distal end of an exemplary endoscope.

An alternative device 110, for example, is depicted in FIG. 2A as having a pair of first and second jaws 120, 130 with a respective set of first and second surfaces 122, 132 that, as above, are disposed oppositely along an axis Y-Y. First and second jaws 120, 130 are integral with a cap 113. The proximal end of cap 113 has an adapter 115 that is removably attachable to a distal end 100D of an endoscope 100, as depicted in FIG. 2C. At least the distal portions of cap 113 are preferably made of a transparent biocompatible polymer so that the orientation of jaws 120 and 130 relative to distal end 100D may be readily confirmed by the user. For example, the user may deploy an imaging component of endoscope 100 to visualize both the tissue site and the orientation of jaws 120 and 130. Adapter 115 is a flexible annulus configured to secure device 110 on endoscope 100 by imparting a radial compressive force on the exterior surface of distal end 100D. To avoid damaging distal end 100D, adapter 115 is preferably made of a biocompatible elastomer material, like silicone.

Similar to above, second surface 132 of device 110 defines an orifice 140 that is configured to direct a fluid towards first surface 122 so as to move at least the proximal end 4 of portion of tissue 3 (e.g., FIG. 1) toward first surface 122. As best shown in FIG. 2B, a nozzle 142 is mounted in orifice 140 and attached to a fluid delivery channel 144 that extends proximally towards a fluid source (not shown). Second surface 132 and a distal or second edge 134 of second jaw 130 are also configured to guide proximal end 4 of said portion of tissue 3 (FIG.1) over nozzle 142. In FIG. 2C, for example, second surface 132 and distal edge 134 form a scoop with a sharpened edge configured to puncture, separate, and guide portion of tissue 3 as described above.

Figure 4A:
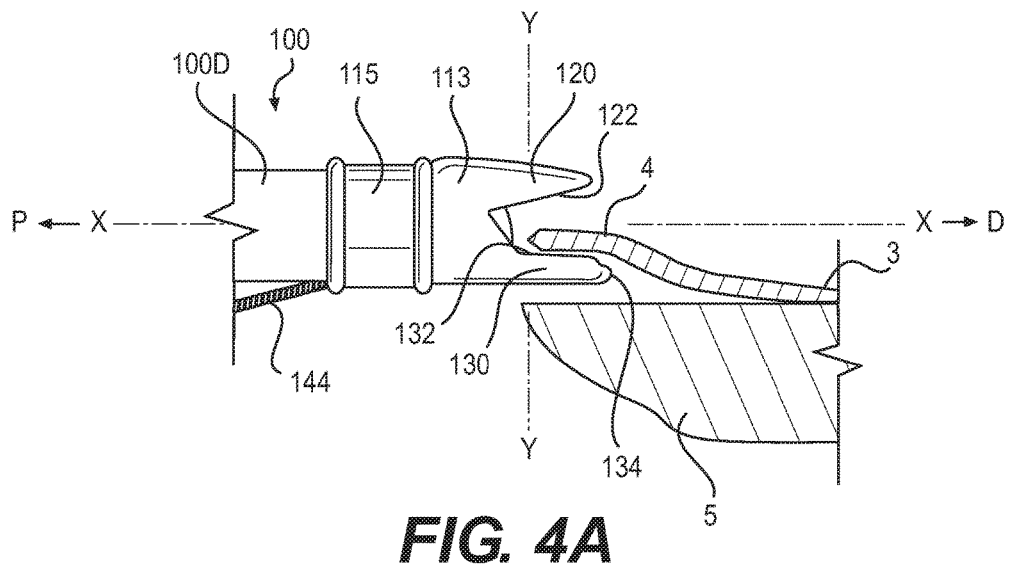
FIG. 4A depicts an exemplary embodiment of the present disclosure that has been placed between a portion of tissue, such as a mucosa, and an underlying portion of tissue, such as a submucosa.
Figure 4B:
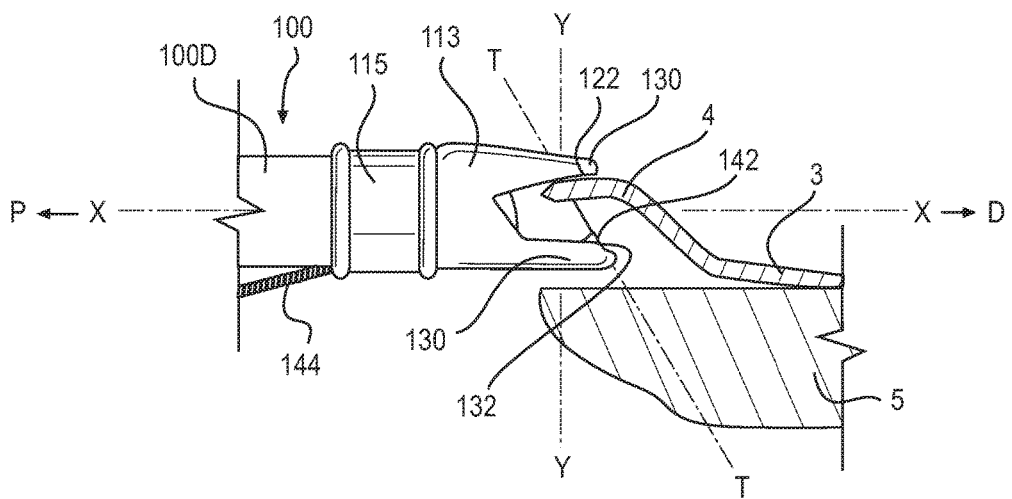
FIG. 4B depicts the embodiment of FIG. 4A after the portion of tissue has been manipulated.

Nozzle 142 is also configured to form the fluid into a rapid stream or jet that flows along a direction of travel T-T. As shown in FIG. 4B, for example, nozzle 142 provides a direction of travel T-T that is transverse to axis Y-Y so as to increase the tensile force applied to portion of tissue 3. A distal edge 124 of first jaw 120 is offset proximally from distal edge 134 of second jaw 130 along in FIG. 2B to ensure that first surface 122 is positioned as a shield inline with direction of travel T-T. Endoscope 100 of FIG. 2C has a plurality of working channels 102. At least one channel 102 may house a cutting tool for resection, such as a blade or a snare that extends out of said channel 102 in a direction parallel to axis X-X. Other working channels 102 may house other surgical tools, such as those specific to visualization, imaging, light, aspiration, irrigation, or the insertion of other instruments. A distal face 112 of cap 113 in FIGS. 2A-C has an opening 117 that defines a central lumen of cap 113 sized to receive the distal end 100D of endoscope 100. Opening 117 surrounds each working channel 102 and, thus, permits full utilization of any component housed within any working channel 102 while distal end 100D is received in opening 117 of cap 113. For example, opening 117 of FIG. 2B is sized to receive said cutting tool therethrough.

Figure 3A:
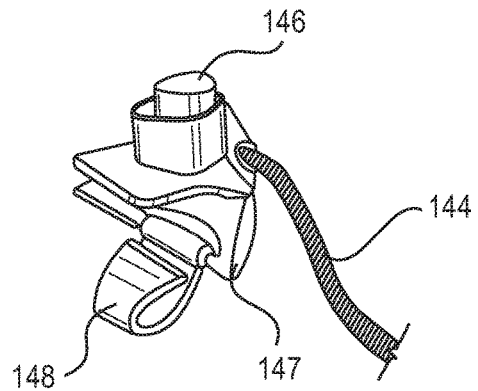
FIG. 3A depicts an exemplary switch having a frame that is removably attachable an elongated tool or endoscope.
Figure 3B:
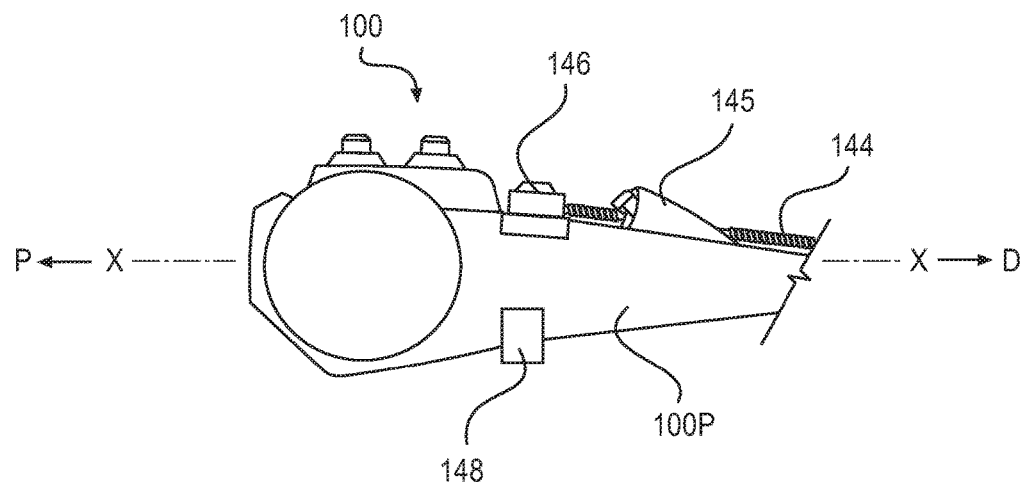
FIG. 3B depicts the switch of FIG. 3A after the frame has been removably attached to a proximal end of an exemplary endoscope.

Fluid flow through orifice 140 is controlled by a switch 146, which, for example, is depicted in FIGS. 3A-B as having a frame 147 that is removably attachable to the proximal end 100P of endoscope 100. Fluid delivery channel 144 extends proximally from orifice 140, along an exterior surface of endoscope 100, and through a stabilizer 145 before attachment to switch 146. This configuration allows the plurality of working channels 102 to remain unoccupied by device 110, thereby allowing any channel 102 to be used with another tool, as noted above. Frame 147 is rotatably attached to a locking clasp 148 that is biased towards a closed position. To attach switch 146 onto proximal end 100P, as depicted in FIG. 3B, clasp 148 is rotated into an open position, wrapped around a portion of proximal end 100P, and then released. Desirably, this configuration allows switch 146 to be form fit onto proximal end 100P so that the user may operate switch 146 with the same hand used to grasp end 100P.

Many features described above may be varied without departing from this disclosure. Orifice 40, for example, may be configured to direct the fluid without nozzle 42, depending upon the type of fluid flowing therethrough. Alternatively, nozzle 42 may be embodied as a plurality of nozzles, each nozzle 42 being separately configured to manipulate portion of tissue 3. For example, one set of nozzles 42 may be used to separate said portion of tissue 3 from underlying portion of tissue 5, while another set of nozzles 42 is used to pin said portion of tissue 3 against first surface 22, and yet another set of nozzles 42 is used to resect proximal end 4 away from said portion of tissue 3. Any embodiment of switch 146 may be modified to control said fluid flows.

In another alternative embodiment, one of the working channels 102 of endoscope 100 may be engageable with fluid delivery channel 144. For example, a shortened embodiment of delivery channel 144 may extend proximally from cap 115 into one of said working channels 102, which may then be used to deliver the fluid. Another one of the working channels 102 may be an exit or vacuum port configured to remove at least a portion of the fluid. First surface 122 may be configured to direct the fluid through opening 117 and into said exit or vacuum port, at least prior to insertion of portion of tissue 3. Although described above as a liquid, such as water, any embodiment of device 10 may be alternatively be configured for use with another force transfer medium. For example, orifice 40 could be alternatively configured to move portion of tissue 3 with a stream of gas, such as air, water vapor, or the like.

A number of methods are also disclosed. For example, an exemplary method of using device 110 to manipulate tissue 3 is disclosed with reference to FIGS. 4A-B. This method comprises the initial step of attaching adapter 115 to a distal end 100D of endoscope 100. Additional method steps comprise placing device 110 near portion of tissue 3 and, as shown in FIG. 4A, guiding portion of tissue 3 over orifice 140. Distal edge 134 of second jaw 132 may be moved distally to separate portion of tissue 3 from underlying tissue 5, while second surface 132 may be used to guide the proximal end 4 of said portion of tissue 3 over orifice 140, as described above. Either distal edge 134 or another device may be used to puncture the portion of tissue 3, thereby permitting second jaw 130 to separate said portion of tissue 3 from underlying tissue 5. Another method step comprises flowing a fluid out of the orifice 140, or nozzle 142, towards first surface 122 so as to move portion of tissue 3 toward first surface 122. Switch 146 may be operated to cause or control the fluid flow, depending upon the desired fluid pressure. In some embodiments, the proximal end 4 of portion of tissue 3 may be pinned or otherwise forced against first surface 122 by the jet so as to apply a tensile force to the portion tissue 3 that makes resection easier.

A similar method may be used to resect proximal end 4 from portion of tissue 3. Any cutting tool may be used to perform the resection. For example, device 110 may have a distal face 112 with an opening 117 sized to receive a cutting tool, thereby enabling the step of extending the cutting tool distally through opening 117 to perform the resection. If endoscope 100 has at least one working channel 102, then this method may comprise extending the cutting tool distally out of said working channel 102 and through opening 117 to perform the resection. Additional method steps may comprise extending another surgical tool out of one of the working channels 102 to aid in resection, such as tools for visualization, imaging, light, aspiration, irrigation, tool insertion, or the like.

Figure 5:
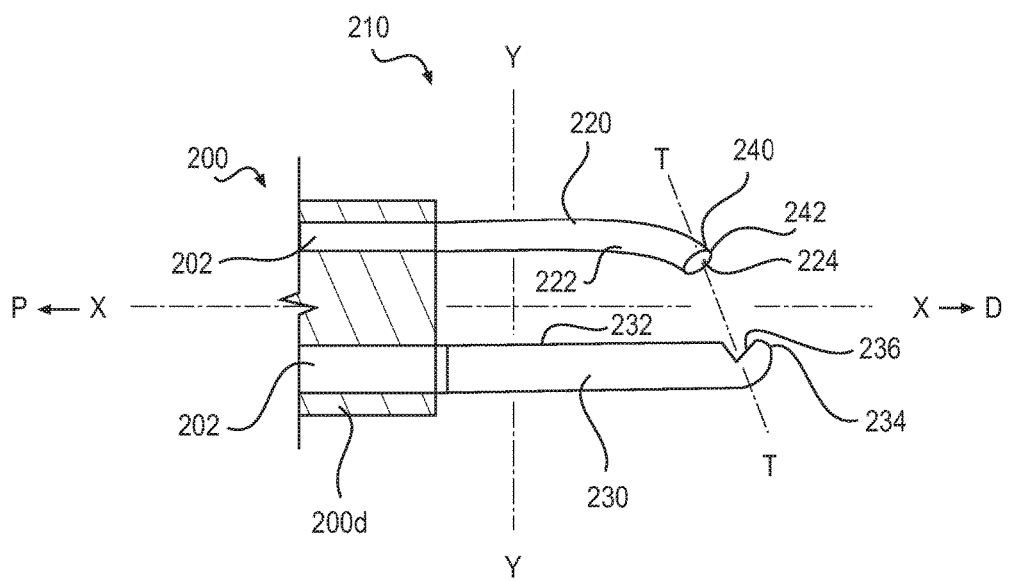
FIG. 5 depicts an exemplary embodiment of the present disclosure that is extendable from a distal end of an elongated tool or endoscope.

An alternative device 210 is depicted in FIG. 5. Device 210 has a pair of first and second jaws 220 and 230 with a respective set of first and second surfaces 222 and 232 that, as above, are disposed oppositely along an axis Y-Y. In contrast to above, device 210 has first jaw 220 with a distal edge 224 that defines an orifice 240 configured to direct a fluid towards second surface 232. Each of jaws 220 and 230 are shown as being extendable from a working channel 202 of endoscope 200. A nozzle 242 is mounted in orifice 240 of FIG. 5. As before, nozzle 242 may be used to form the fluid into a jet that flows along a direction of travel T-T to move the proximal end 4 of said portion of tissue 3 (e.g., FIG. 1) towards second surface 232. Nozzle 242 of FIG. 5 may be configured to deliver the fluid at a pressure sufficient to separate proximal end 4 from portion of tissue 3. For example, nozzle 242 may be configured to form the fluid into a small and powerful (e.g., ultrasonic) water-jet configured to cut portion of tissue 3. The fluid pressure applied by the jet is relative to the type of tissue. For esophageal or stomach tissue, the fluid pressure may be about 435 PSI (or 30 Bar) to about 725 PSI (or 50 Bar) to ensure that portion of tissue 3 is cut cleanly. For the left colon, the fluid pressure may be about 290 PSI (or 20 Bar) to about 435 PSI (or 30 Bar); whereas, for the right colon, the fluid pressure may be about 145 PSI (or 10 Bar) to about 218 PSI (or 15 Bar). These values are, of course, exemplary.

Jaw 220, or any counterpart element, may be a distal end of a tube having a fluid delivery channel embodied as a lumen for delivering fluid to the distal end. The tube and its distal end may be flexible, steerable, and articulable to, for example, aim nozzle 242 in a desired location, with or without the aid of guidance, visual or otherwise, from another surgical tool. Similar to above, second surface 232 may act as a shield positioned opposite of the jet to prevent it from cutting deeper than, for example, a mucosa tissue layer. Surface 232, like the aforementioned tube, may also be flexible, steerable, and articulable so as to ensure that the jet remains shielded if nozzle 242 is aimed. Aside from preventing tissue damage, this shielding feature may also reduce the risk of cancer seeding by preventing any cut parts of tissue 3 from spreading outwardly. Although not required, second surface 232 is depicted as having notch 236 with a fluid receiving surface that is transverse to direction of travel T-T. Notch 236 may be used to concentrate the application of fluid pressure against portion of tissue 3.

Methods for using device 210 are also disclosed. An initial method step comprises extending the first and second jaws 220 and 230 out of a working channel 202 of endoscope 200. Other method steps comprise placing second jaw 230 adjacent portion of tissue 3, and guiding portion of tissue 3 towards orifice 240. As before, a distal edge 234 of second jaw 230 may be moved distally to separate, puncture, or otherwise move portion of tissue 3 away from underlying tissue 5. Second surface 232 may then be used to guide portion of tissue 3 towards a distal face 212 of endoscope 200. Another method step comprises flowing a fluid out of the orifice 240, or nozzle 242, and towards second surface 232 so as to cut portion of tissue 3. The fluid pressure may be varied according to this method. For example, the fluid may be delivered at a lower pressure to move portion of tissue 3 towards distal face 212, and then throttled to a higher pressure through nozzle 242 to perform the resection. A switch, like switch 146, may be operated to control the fluid flows.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

We claim:

1. A medical device for manipulating a portion of tissue and configured to be coupled to an endoscope, the device comprising:
a distal end with a first jaw having a first surface and a second jaw having a second surface, the first surface being diametrically opposite of the second surface about a longitudinal axis of the endoscope so as to define a tissue receiving opening sized to receive a tool extending distally from a distal end of the endoscope when the medical device is coupled to the endoscope, the second surface having a distal edge insertable between the portion of tissue and an underlying portion of tissue, wherein the distal end of the medical device is configured to be removably coupled to the distal end of the endoscope;
a proximal end including a switch, wherein the proximal end is configured to be removably coupled to a proximal portion of the endoscope;
a fluid delivery channel extending between the proximal and distal ends of the medical device, wherein the fluid delivery channel is configured to be positioned outside of the endoscope; and
an orifice defined by the second surface and configured to direct a fluid towards the first surface so as to move the portion of tissue towards the first surface.

2. The device of claim 1, wherein a position of the first jaw is fixed relative to a position of the second jaw.

3. The device of claim 1, wherein the distal edge is configured to guide a proximal end of said portion of tissue into the receiving opening when the device is moved distally.

4. The device of claim 1, wherein the orifice has one or more nozzles that form the fluid into a jet, and the distal edge is configured to guide the proximal end of said portion of tissue over the jet.

5. The device of claim 4, wherein the fluid pressure applied to the portion of tissue by the jet is adjustable.

6. The device of claim 4, wherein the jet has a direction of travel that is transverse to the axis so as to force the portion of tissue towards the first surface and apply a tensile force to the portion of tissue by moving a proximal end of said portion of tissue in the direction of travel.

7. The device of claim 1, wherein the first and second jaws are integral with a cap having an adapter that is removably engageable with the distal end of the endoscope.

8. The device of claim 7, wherein the first surface is configured to direct the fluid proximally towards the opening of the cap proximal end.

9. The device of claim 1, wherein the fluid delivery channel is coupled to a fluid source, and wherein the fluid source is operably attached to a fluid pump that is operated in response to the switch.

10. A medical device for resecting a portion of tissue and configured to be coupled to an endoscope, the device comprising:
a distal end with a first jaw having a first surface and a second jaw having a second surface, the first surface being diametrically opposite of the second surface about a longitudinal axis of the endoscope so as to define a space sized to receive a tool extending distally from a distal end of the endoscope when the medical device is coupled to the endoscope, the second surface having a distal edge configured to be placed between the portion of tissue and an underlying portion of tissue, wherein the distal end of the medical device is configured to be removably coupled to the distal end of the endoscope;
an orifice defined by the second surface and configured to direct a fluid towards the first surface so as to move the portion of tissue towards the first surface;
a proximal end;
a fluid delivery channel that extends between the orifice and the proximal end of the medical device for attachment to a fluid source, wherein the fluid delivery channel is configured to be positioned outside of the endoscope; and
a switch that is operable to flow the fluid from the fluid source, through the delivery channel, and out of the orifice, wherein the switch is configured to be removably coupled to a proximal portion of the endoscope.

11. The device of claim 10, wherein the orifice has one or more nozzles that form the fluid into a jet, and the distal edge is configured to guide the proximal end of said portion of tissue over the jet.

12. The device of claim 11, wherein the first and second jaws are integral with a cap having an adapter that is removably engageable with the endoscope and a proximal end sized to receive the tool extending proximally from a working channel of the endoscope.

13. A medical device for manipulating a portion of tissue and configured to be positioned on an endoscope, the device comprising:
a distal end with a first jaw having a first surface and a second jaw having a second surface, the first surface being diametrically opposite of the second surface about a longitudinal axis of the endoscope when the medical device is coupled to the endoscope, wherein the distal end is configured to be removably coupled to a distal portion of the endoscope, wherein the distance between the first surface and the second surface is sized to receive a tool extending distally from a distal end of the endoscope when the medical device is coupled to the endoscope;
a proximal end including a switch, wherein the proximal end is configured to be removably coupled to a proximal portion of the endoscope;
a fluid delivery channel extending between the proximal and distal ends of the medical device, wherein the fluid delivery channel is configured to be positioned outside of the endoscope; and
an orifice defined by the second surface and configured to direct a fluid towards the first surface so as to move the portion of tissue towards the first surface.

14. The device of claim 13, wherein a position of the first jaw is fixed relative to a position of the second jaw.

15. The device of claim 13, wherein the orifice has one or more nozzles that form the fluid into a jet, and the second surface is configured to guide the proximal end of said portion of tissue over the jet.

16. The device of claim 15, wherein a fluid pressure applied to the portion of tissue by the jet is adjustable.

17. The device of claim 15, wherein the jet has a direction of travel that is transverse to a longitudinal axis of the first jaw so as to force the portion of tissue towards the first surface and apply a tensile force to the portion of tissue by moving a proximal end of said portion of tissue in the direction of travel.

18. The device of claim 13, wherein the first and second jaws are integral with a cap having:
an adapter that is removably engageable with the distal end of at least one other medical device; and a cap proximal end sized to receive the tool extending distally from said distal end of the endoscope.

19. The device of claim 13, wherein the fluid delivery channel is coupled to a fluid source, and the switch is operable to flow the fluid from the source, through the delivery channel, and out of the orifice.

20. The device of claim 19, wherein the fluid source is operably attached to a fluid pump that is operated in response to the switch.

* * * * *